United States Patent
Dettinger et al.

(10) Patent No.: US 11,301,809 B2
(45) Date of Patent: **\*Apr. 12, 2022**

(54) CARE PLAN ADMINISTRATION

(71) Applicant: Preventice Solutions, Inc., Rochester, MN (US)

(72) Inventors: Richard D. Dettinger, Rochester, MN (US); Richard M. Smith, Oronoco, MN (US); Scott J. Burrichter, Rochester, MN (US)

(73) Assignee: Preventice Solutions, Inc., Rochester, MN (US)

( * ) Notice: Subject to any disclaimer, the term of this patent is extended or adjusted under 35 U.S.C. 154(b) by 305 days.

This patent is subject to a terminal disclaimer.

(21) Appl. No.: 16/714,169

(22) Filed: Dec. 13, 2019

(65) Prior Publication Data

US 2020/0118673 A1  Apr. 16, 2020

Related U.S. Application Data

(63) Continuation of application No. 16/121,470, filed on Sep. 4, 2018, now Pat. No. 10,510,444, which is a
(Continued)

(51) Int. Cl.
*G06Q 10/10* (2012.01)
*G16H 40/63* (2018.01)
(Continued)

(52) U.S. Cl.
CPC .............. *G06Q 10/10* (2013.01); *G16H 20/60* (2018.01); *G16H 40/20* (2018.01); *G16H 40/63* (2018.01);
(Continued)

(58) Field of Classification Search
CPC ........ G06Q 50/22; G06Q 50/24; G06Q 10/10; G06F 19/00; G06F 19/30; G06F 19/32;
(Continued)

(56) References Cited

U.S. PATENT DOCUMENTS 6,188,407 B1  2/2001  Smith et al.
6,632,180 B1  10/2003  Laragh
(Continued)

FOREIGN PATENT DOCUMENTS

WO  2007117719 A2  10/2007
WO  2014/116968 A1  7/2014
WO  2016057728 A1  4/2016

OTHER PUBLICATIONS

Tafreshi et al., Automated analysisofECGwaveformswithatypicalQRScomplex morphologies, Biomedical Signal Processing and Control vol. 10 (2014) p. 41-49.
(Continued)

*Primary Examiner* — Jason S Tiedeman
(74) *Attorney, Agent, or Firm* — Faegre Drinker Biddle & Reath LLP

(57) ABSTRACT

Techniques for administering a care plan. Biometric data collected by a monitoring device is received at a care plan management system using a communication network. The biometric data includes a first event classified by a remote device as a first type of event. A relative processing priority for the first event is determined, at the care plan management system, based on the first type. The first event is processed, at the care plan management system, based on the relative processing priority. The processing includes re-classifying the first event as a second type of event. The re-classification is more computationally intensive than the classification by the remote device. At least one treatment task specified in the care plan is initiated, using a computer processor, and based on the re-classified first event.

20 Claims, 10 Drawing Sheets

Related U.S. Application Data continuation of application No. 14/508,472, filed on Oct. 7, 2014, now Pat. No. 10,095,841.

(51) Int. Cl.
| | | |
|---|---|---|
| *G16H 50/20* | (2018.01) | |
| *G16H 40/67* | (2018.01) | |
| *G16H 20/60* | (2018.01) | |
| *G16H 40/20* | (2018.01) | |
| *A61B 5/318* | (2021.01) | |

(52) U.S. Cl.
CPC ............ *G16H 40/67* (2018.01); *G16H 50/20* (2018.01); *A61B 5/318* (2021.01)

(58) Field of Classification Search
CPC .... G06F 19/325; G06F 19/34; G06F 19/3475; G06F 19/3406; G06F 19/3418; G06F 19/345; G06F 19/36; G16H 10/00; G16H 10/60; G16H 15/00; G16H 20/00; G16H 20/60; G16H 40/20; G16H 40/60; G16H 40/63; G16H 40/67; G16H 50/00; G16H 50/20; G16H 50/22; G16H 50/70; A61B 5/00; A61B 5/0004; A61B 5/0006; A61B 5/02; A61B 5/021; A61B 5/02108; A61B 5/024; A61B 5/02438; A61B 5/0245; A61B 5/0402
USPC .......................................................... 705/2, 3
See application file for complete search history.

(56) References Cited

U.S. PATENT DOCUMENTS

| | | | |
|---|---|---|---|
| 7,702,382 | B2 | 4/2010 | Xue et al. |
| 7,751,873 | B2 | 7/2010 | de Voir |
| 8,478,389 | B1 | 7/2013 | Brockway et al. |
| 8,521,269 | B1* | 8/2013 | Gunderson ........... A61N 1/3621 600/518 |
| 10,095,841 | B2 | 10/2018 | Dettinger et al. |
| 2002/0026103 | A1 | 2/2002 | Norris et al. |
| 2002/0029157 | A1 | 3/2002 | Marchosky |
| 2002/0184050 | A1 | 12/2002 | Papageorge |
| 2005/0131741 | A1 | 6/2005 | Tang et al. |
| 2006/0025696 | A1 | 2/2006 | Kurzweil et al. |
| 2006/0025697 | A1 | 2/2006 | Kurzweil et al. |
| 2006/0053034 | A1 | 3/2006 | Hlathein et al. |
| 2006/0217621 | A1* | 9/2006 | Kim ........................ A61B 5/35 600/509 |
| 2006/0287885 | A1 | 12/2006 | Frick |
| 2006/0293573 | A1 | 12/2006 | Bardy |
| 2007/0123788 | A1 | 5/2007 | Gunderson et al. |
| 2007/0255594 | A1 | 11/2007 | Muehlmeier et al. |
| 2008/0126124 | A1 | 5/2008 | Schechter |
| 2008/0183496 | A1 | 7/2008 | Dunham et al. |
| 2010/0298664 | A1 | 11/2010 | Baumann et al. |
| 2011/0021934 | A1 | 1/2011 | Kim et al. |
| 2011/0112418 | A1 | 5/2011 | Feild et al. |
| 2011/0125519 | A1 | 5/2011 | Dhoble |
| 2011/0161107 | A1 | 6/2011 | Goldberg et al. |
| 2011/0167250 | A1 | 7/2011 | Dicks et al. |
| 2011/0179405 | A1 | 7/2011 | Dicks et al. |
| 2011/0208079 | A1* | 8/2011 | Babaeizadeh ......... A61B 5/361 600/518 |
| 2011/0276338 | A1 | 11/2011 | Warner et al. |
| 2011/0313786 | A1 | 12/2011 | Fishman |
| 2012/0101847 | A1 | 4/2012 | Johnson et al. |
| 2013/0083054 | A1 | 4/2013 | Bayouk |
| 2013/0149683 | A1 | 6/2013 | Steerman |
| 2013/0179178 | A1 | 7/2013 | Vemireddy et al. |
| 2013/0198531 | A1 | 8/2013 | Hansen et al. |
| 2013/0231947 | A1 | 9/2013 | Shusterman |
| 2014/0156291 | A1 | 6/2014 | Kozicki et al. |
| 2014/0257838 | A1 | 9/2014 | Karra et al. |
| 2014/0257852 | A1 | 9/2014 | Walker et al. |
| 2014/0303989 | A1 | 10/2014 | Ferguson |
| 2014/0324445 | A1 | 10/2014 | Carlsgaard et al. |
| 2015/0051918 | A1 | 2/2015 | Kehoe et al. |
| 2015/0154528 | A1 | 6/2015 | Kharraz Tavakol |
| 2015/0193295 | A1 | 7/2015 | Boger |
| 2015/0199010 | A1 | 7/2015 | Coleman et al. |
| 2015/0234996 | A1 | 8/2015 | Wartena et al. |
| 2015/0265164 | A1 | 9/2015 | Gopalakrishnan et al. |
| 2015/0359489 | A1 | 12/2015 | Baudenbacher et al. |
| 2018/0347576 | A1 | 12/2018 | Juh et al. |

OTHER PUBLICATIONS

Elgendi et al., Revisiting QRS Detection Methodologies for Portable, Wearable, Battery-Operated, and Wireless ECG Systems, PLoS ONE vol. 9, Issue 1, e84018, Jan. 2014, 18 pages.

Zhou et al., "Real-Time Automatic ECG Diagnosis Method Dedicated to Pervasive Cardiac Care," Wireless Sensor Network, 2009, 1, 276-283.

International Search Report for PCT/US2015/054575, dated Feb. 19, 2016.

* cited by examiner

| | 🔍 //interface/ | | | | _ ☐ ✕ |
|---|---|---|---|---|---|
| Patient Name: 405 | | Patient ID: 410 | | Condition: 415 | |
| Doe, John | | 1-12345-678 | | High Blood Pressure | |

| Task | Frequency |
|---|---|
| Wear sensor | As directed |
| Take blood pressure | Once a day |
| Take 60 milligrams of aspirin | Every morning |

420 — 425

▲
▼

Threshold Set 1: Weekly Weight — 430

| Type | Value | Warning Level | Symptoms | Alert Type | Delete |
|---|---|---|---|---|---|
| Gain | 2.5 kg | Tier 2 | Multiple symptoms selected | Chat | X |
| Loss | 2.5 kg | Tier 1 | Any | Chat | X |

Add

Threshold Set 1: Weekly Weight

| Type | Value | Warning Level | Symptoms | Alert Type | Delete |
|---|---|---|---|---|---|
| Not received | - - - | Tier 3 | Any | Chat | X |
| Less than | < 90 | Tier 2 | None | Chat | X |
| Greater than | > 120 | Tier 2 | Racing heart, light headed | Chat | X |

Add

Add Threshold Set

Cancel  Save

FIG. 4

CARE PLAN ADMINISTRATION

CROSS-REFERENCE TO RELATED APPLICATIONS

This application is a continuation of U.S. patent application Ser. No. 16/121,470, filed Sep. 4, 2018, which is a continuation of United States Parent application Ser. No. 14/508,472, filed Oct. 7, 2014. The above-referenced applications are hereby incorporated by reference in their entirety.

BACKGROUND

Field

Embodiments presented herein generally describe techniques related to health care, and more specifically, for administering an individualized care plan for a patient.

Description of the Related Art

In the health care field, a care plan is a set of tasks provided by a health care practitioner (e.g., a doctor) to a patient. Historically, care plans are a written document that provides directions and routines for a patient to follow to manage certain health conditions. The care plan may include a set of tasks (e.g., exercise for a given duration) for the patient to perform, content that educates the patient about a diagnosed condition (e.g., brochures describing the diagnosed condition), and logs for the patient to periodically record information in (e.g., weight, blood pressure, etc.). As an example, a doctor might create a care plan for a patient with hypertension that includes several brochures describing hypertension and hypertension treatment and assigned tasks such as walking on a treadmill for thirty minutes each morning, drinking a glass of water every three hours, and recording blood pressure at the end of each day. Thus, as part of the treatment of the condition, the patient is expected to adhere to the tasks listed in the care plan and to then follow up with the doctor in a subsequent appointment to assess the patient's progress.

The current care plan approach has several shortcomings. For instance, a care plan for a particular condition is often tailored towards the condition itself, without considering relevant details about a patient. Typically, once a doctor has diagnosed a patient with a particular condition, the doctor prints out a "one size fits all" care plan for the individual that instructs the individual on how to manage the condition. Although the doctor may include notes in the printed pamphlet describing the care plan, the doctor is often unable to modify the care plan otherwise (e.g., to craft the care plan specifically for the patient). Further, a healthcare provider often has no way of determining the patient's adherence to the care plan until a follow-up appointment. Currently, to address this concern, care providers rely on the patient's own testimony as to their adherence (e.g., using an exercise log). Additionally, providers may employ call centers to contact the patient periodically and determine whether the patient is following the care plan. However, such an approach is costly and further exposes a patient's information to more individuals than necessary.

SUMMARY

Embodiments include a method for administering a care plan. The method includes receiving, at a care plan management system using a communication network, biometric data collected by a monitoring device and including a first event classified by a remote device as a first type of event. The method further includes determining, at the care plan management system, a relative processing priority for the first event based on the first type. The method further includes processing the first event, at the care plan management system, based on the relative processing priority, the processing including re-classifying the first event as a second type of event. The re-classification is more computationally intensive than the classification by the remote device. The method further includes initiating at least one treatment task specified in the care plan, using a computer processor, and based on the re-classified first event.

Embodiments further include a non-transitory computer-readable medium containing computer program code that, when executed, performs an operation for administering a care plan. The operation includes receiving, at a care plan management system using a communication network, biometric data collected by a monitoring device and including a first event classified by a remote device as a first type of event. The operation further includes determining, at the care plan management system, a relative processing priority for the first event based on the first type. The operation further includes processing the first event, at the care plan management system, based on the relative processing priority. The processing includes re-classifying the first event as a second type of event. The re-classification is more computationally intensive than the classification by the remote device. The operation further includes initiating at least one treatment task specified in the care plan, based on the re-classified first event.

Embodiments further include a system for administering a care plan. The system includes a monitoring device, a care plan management system, and a mobile device that facilitates communication between the monitoring device and the care plan management system. The care plan management system is configured to receive, using a communication network, biometric data collected by the monitoring device and including a first event classified as a first type of event by at least one of the monitoring device or the mobile device. The care plan management system is further configured to determine a relative processing priority for the first event based on the first type. The care plan management system is further configured to process the first event based on the relative processing priority. The processing including re-classifying the first event as a second type of event. The re-classification is more computationally intensive than the classification as the first type of event. The system is configured to initiate at least one treatment task specified in the care plan, based on the re-classified first event.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIG. 4 illustrates a task view of the care protocol template described in FIG. 3, according to one embodiment.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
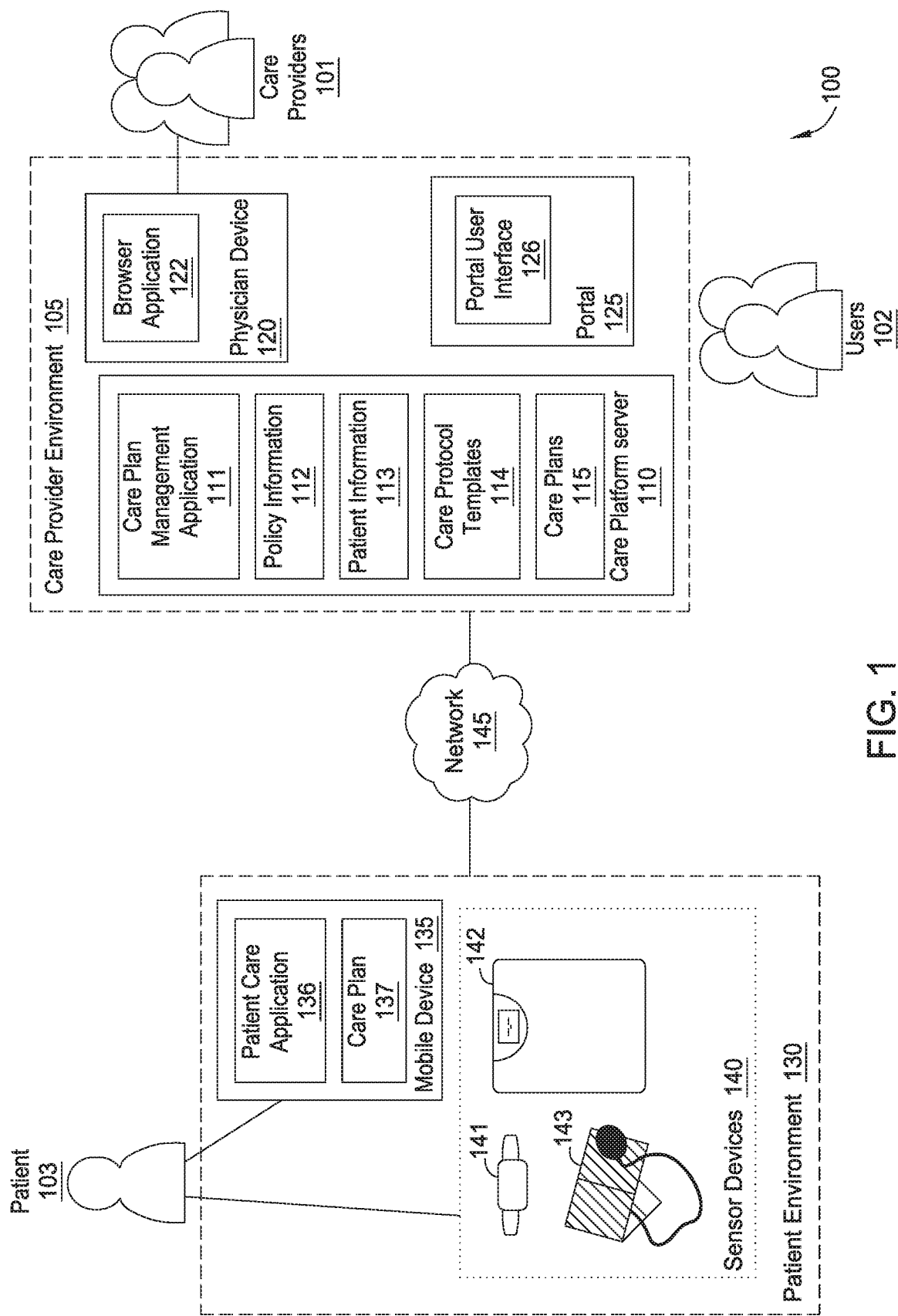
FIG. 1 illustrates an example computing environment, according to one embodiment.

Current approaches for providing a care plan for a patient to follow and monitoring the patient's adherence are rigid. For example, in many cases, a physician who has diagnosed a patient with a particular condition may provide the patient with a generalized care plan commonly used to address that condition, e.g., pre-printed documents that are not tailored to any particular patient but rather generally address the diagnosed medical condition. As a result, such printed care plans do not allow the physician to customize the care plan beyond annotating the care plan along the physical margins.

Further, to address multiple conditions, a physician typically has to print separate care protocol pamphlets addressing each of multiple medical conditions the patient has been diagnosed with. Manually annotating each of the pre-printed documents is particularly inconvenient when the physician must reconcile multiple care protocols for multiple different medical conditions the patient has been diagnosed with, where treatment recommendations within one of the protocols may differ from or even conflict with the treatment recommendation for another of the care protocols. Additionally, some tasks in each of the printed pamphlets may overlap (e.g., two different care plans may instruct a patient to take a certain dosage of aspirin at a given time of day), a patient may have difficulty understanding the tasks to perform, leading to poor compliance. Moreover, in some situations, the tasks for treating the various diagnosed conditions may conflict with one another, leaving the patient unsure as to how to reconcile the conflict.

Embodiments presented herein describe techniques for administering a customized health care plan for an individual. In one embodiment, a care platform is provided that allows a physician to design a care plan tailored specifically for an individual patient. The care plan may include multiple care plan protocols, with each of the care plan protocols addressing a respective medical condition the patient has been diagnosed with. Generally, a care plan protocol describes the treatment of a particular medical condition. For instance, a care plan could specify a set of specific tasks for a patient to follow to manage the particular medical condition and could divide the tasks by phases and schedules. Generally, different care plan protocols may be available for each of a variety of conditions, such as congestive heart failure, diabetes, sprained ankle, etc.

In addition, the care protocol may specify metrics that the care platform monitors during the patient's treatment, thresholds to detect for each metric, and remedial actions to be taken in response to detecting such thresholds. One example metric is blood pressure. The blood pressure metric may be associated with thresholds indicating values and conditions in which the care platform performs some action in response to detecting such values and conditions, e.g., sending instructions to the patient to rest for a given period of time. Further, the care protocol may provide the patient with resources to educate the patient about a diagnosed condition, treatment, and the like (e.g., instructional videos, articles, etc.).

A physician may assign multiple care plan protocols to a patient suffering from multiple medical conditions. To do so, the physician may configure templates for care plan protocols corresponding to the patient's conditions. Each care protocol template can further provide a general set of tasks to follow for a given condition. In one embodiment, the physician may configure the templates via a user interface provided by the care platform. The physician may customize each template specifically for the patient. For example, assume a care protocol template for congestive heart failure recovery specifies a number of tasks to be performed at a specified interval (e.g., daily), such as walk for fifteen minutes, take prescribed medicine, record blood pressure, and record weight. If the physician deems that the patient is already within a healthy weight, the physician may remove the "record weight" task from the protocol. Further, the physician may also adjust the length of time that the patient should walk. In addition, the physician may insert additional tasks to the protocol.

For example, the care plan could specify an assigned task for a patient to weigh themselves weekly until the patient is out of target weight range. Upon detecting the patient's weight is outside of the target range, the care platform could provide instructions (and potentially a medical prescription, with the approval of the patient's physician) for the patient to follow in order to get the patient's weight back into the target range. Moreover, the care platform could alter the patient's care plan to assign the patient the task of weighing himself daily until the patient's weight has returned to the target range. As another example, the care platform could adjust the duration of the patient's assigned task of walking, based on the patient's ability to get their heart rate into a target zone and to sustain this heart rate, as determined from data collected using one or more monitoring devices during the patient's previous exercise sessions.

Further, the physician may customize metrics specified in the care protocol and thresholds associated with each metric. Continuing the example of a care protocol for congestive heart failure recovery, the care protocol may specify a heart rate metric as well as a threshold that alerts the physician whenever the patient's heart rate is over a value X. In such a case, the physician may adjust the threshold by adding conditions that need to be satisfied before alerting the physician, e.g., in order to trigger an alert due to the patient's heart rate being above a value X, the patient's activity level must be below a value Y.

The care platform may consolidate the configured care plan protocols into one overall care plan for the patient. However, it is possible that some tasks and phases of different care plan protocols overlap. As such, the care platform may perform operations to reconcile any conflicts between care plan protocols as part of the care plan creation. For example, a care plan protocol for high blood pressure and another for diabetes may include a step for walking for ten minutes each day. Both protocols may also include a step for taking two aspirin pills in the morning, and including two separate steps for taking aspirin may yield unintended consequences related to a dosage that the patient should be taking. As such, the care platform could consolidate the two separate tasks into a single task of taking two aspirin pills each morning.

Once created, the care platform may determine a set of monitoring devices to use in collecting data for the observation metrics specified within the care plan. Generally, the care platform can select at least one device for every observation metric to be monitored. Thus, as an example, if a care plan for a patient specifies to monitor the patient's heart rate and weight, the care platform could determine that a heart rate monitoring device and a scale device should be used to collect data for these metrics. In one embodiment, the monitoring devices may be provided to the patient as part of the setup of the care plan. In a particular embodiment, the patient (or care provider) can select any suitable device(s) for collecting data for the specified observation metrics. For example, if the patient already owns a bathroom scale capable of collecting data on the patient's weight and transmitting such data to the care platform, the patient could (e.g., using a graphical user interface of the care platform) specify that the patient's existing scale should be used to collect weight data for the administration of the care plan.

In one embodiment, a mobile device (e.g., a smart phone or tablet device) is used to facilitate communication between the monitoring devices and the care platform server. For example, an application(s) deployed on a mobile device could communicate with each of the monitoring devices (e.g., wirelessly using Bluetooth® communications) to collect monitored data from each of the devices. The application on the mobile device could then transmit the collected data to the care platform server over a communications network (e.g., the Internet). Doing so allows the collected data to be transmitted to the care platform server without requiring each monitoring devices to have a separate connection to the communications network, and thus allows monitoring devices not capable of connecting to the communications network to still be used.

Once the monitoring devices are determined, the care platform can transmit the care plan to the application deployed on the mobile device. Through the device, the patient may access the care plan and understand the tasks to perform. Moreover, information can be provided to the patient through the mobile device as part of the administration of the care plan. For example, such information can be provided via a display device of the mobile device, through one or more speaker devices of the mobile device, other input/output devices of the mobile device or some combination thereof. Examples of such information includes alerts (e.g., provided responsive to a monitored metric exceeding a threshold value), reminders (e.g., when a patient fails to perform an assigned task within a specified window of time), educational content (e.g., instructional videos, audio and/or documents describing how to perform a particular exercise), and so on. Further, the mobile device may receive information from various sensors that monitor patient activity (e.g., heart rate, weight, blood pressure). The application can record the information to the care plan and relay information to the care platform. As a result, the physician can monitor the patient's adherence to the care plan.

In one embodiment, each task set out in the care plan may be associated with an observation threshold, such that when patient activity reaches a particular threshold, the care platform may take a certain action in response, such as notifying the physician. Generally, the set of actions taken in response to an observation threshold being satisfied are referred to herein as a treatment plan. In carrying out the treatment plan, the care platform could first attempt to collect additional information about the patient's condition. For instance, the mobile device may display a graphical user interface asking the patient to select any symptoms the patient is currently having. Based on patient's selection, the mobile device could reference the treatment plan to determine how to appropriately respond to the patient's current condition.

For example, assume that the observation threshold in question relates to the patient's heart rate and that the patient's heart rate is currently above the threshold rate. Upon detecting the patient's heart rate exceeds the threshold, the mobile device could instruct the patient to sit and rest, and could display an interface asking what symptoms (if any) the patient is currently having. In this example, if the patient specifies that he is not currently having any symptoms, the treatment plan could specify to continue monitoring the patient and to determine whether the patient's heart rate remains elevated after a specified period of time (e.g., 15 minutes). On the other hand, if the patient specifies that he is currently experiencing symptoms such as dizziness, sweating, and nausea, the treatment plan could specify to immediately escalate the treatment to a healthcare professional and could generate an alert to the healthcare professional describing the patient's current condition. Doing so enables the care platform to respond appropriately to a variety of different situations.

As discussed above, the care plan could perform treatment operations responsive to detecting an observation metric that exceeds a threshold value, before escalating to a physician or emergency services. For example, upon detecting the patient's heart rate exceeds a threshold value while the patient's overall activity level is relatively low, the care platform could present the patient with instructions (e.g., via the mobile device) to sit and rest for a period of time. If the patient's heart rate remains elevated after the patient has complied with the instructions, the care platform could then determine that more urgent treatment is needed and could alert emergency services as to the patient's condition. As stated, the physician may create, edit, or remove observation thresholds while configuring a care protocol template. For example, for a task that requires a patient to record a daily weight, the physician may specify a threshold weight gain at which to generate an alert, e.g., if the patient gains two pounds after a day.

FIG. 1 illustrates an example computing environment 100, according to one embodiment. As shown, the computing environment 100 may include a care provider environment 105 and a patient environment 130, each connected to one another via a network 145. The environments 105 and 130 allow a patient 103 to communicate with a care provider 101 (e.g., a physician).

The care provider environment 105 includes a care platform server 110, a physician device 120, and a portal 125. Each of the care platform server 110, physician device 120, and portal 125 may be a physical computing system or may be a virtual computer instance (e.g., executing in a cloud computing platform). A care provider 101 may use the physician device 120 to access (e.g., via a browser application 122) a portal user interface 126 hosted by the portal 125.

The portal user interface 126 itself provides users 102 (e.g., the care providers 101, the patient, authorized members of the patient's family, etc.) with access to the care platform server 110.

The care platform server 110 includes various applications and data that allow a care provider 101 to create and manage a care plan for a patient 103. As shown, the care platform server 110 includes a care plan management application 111, policy information 112, patient information 113, care protocol templates 114, and care plans 115. The care plan management application 111 generates care plans 115 based on care protocol templates 114.

A care plan 115 may be created based on one or more care protocols, with each of the care protocols relating to a respective medical condition the patient has been diagnosed with. A care protocol is a set of tasks that a patient 103 follows to manage a certain condition, metrics that the care plan management application 111 monitors, objectives for the patient to meet, and the like. For instance, a care protocol may target recovery from a heart attack. Another care protocol may treat diabetes. Tasks associated with a care protocol may include steps such as exercising for a specified duration or taking medication at a certain time of day.

Further, each care plan protocol may be divided into different phases. The phases may represent different stages of care for a particular condition, e.g., a recovery phase, a maintenance phase, etc., where each phase may include a respective set of tasks for the patient to perform, observation metrics to monitor, observation thresholds to detect when the monitored metrics satisfy specified conditions. For example, a care protocol for weight management may include several phases. A patient 103 may begin the care protocol at a weight loss phase, where tasks may include performing strenuous exercises frequently, and where thresholds may specify further actions that the care plan management application 111 takes if the patient 103 loses X amount of weight or gains Y amount of weight. For example, if the metrics indicate that the patient 103 gained Y amount of weight after a period at which the patient 103 had a Z average activity level, the care plan management application 111 may instruct the patient 103 to watch an educational video in response. Continuing the example, if the patient 103 loses X amount of weight during a given period, the care plan management application 111 may transition the care protocol to a weight maintenance phase, where tasks may include exercises that assist the patient 103 in maintaining the weight.

Each care plan protocol may also include observation thresholds associated with monitored metrics and could further specify an action(s) to be taken responsive to an observation threshold being satisfied. The care platform server 110 may monitor the adherence of a patient 103 through various sensor devices 140 that can measure heart rate, weight, blood pressure, and the like. The care platform server 110 may take specified actions if one of the metrics crosses a corresponding threshold, e.g., if a patient 103 gains 1.5 pounds after a day, the platform server 110 may report the weight gain to the care provider 101.

To generate a care plan, a care provider 101 may configure care protocol templates 114 corresponding to medical conditions the patient 103 is diagnosed with. To do so, the care provider 101 (e.g., via the portal user interface 126) selects one or more care protocol templates 114 to associate with the patient 103. The care plan management application 111 populates a care plan with tasks, triggers, and monitoring thresholds as specified by the selected care protocol templates 114. The portal user interface 126 may display the selected care protocol templates 114, where the care provider 101 may customize various facets of each selected template 114, such as tasks and thresholds. For example, the care provider 101 may customize a task instructing a patient to check blood pressure every morning. The care provider 101 may adjust the task so that the patient checks blood pressure twice a day. In addition, the care provider 101 may adjust thresholds associated with that task, such that the care platform server 110 alerts the care provider 101 if a threshold blood pressure is reached.

In one embodiment, each customization may be subject to comply with policy information 112 and such compliance may be enforced by the care plan management application 111 during the creation of the care plan. Policy information 112 may include various guidelines (e.g., set by a hospital, standards organization, insurance companies, etc.) that each care protocol must adhere to. For instance, the policy information 112 may specify milligram ranges for certain medications that may be assigned to a patient 103 in a care protocol. The care plan management application 111 may enforce such policy information 113 to ensure a care provider 101 configuring a care plan does not customize tasks beyond the bounds of the policy information 113.

The care plan management application 111 generates a care plan 115 for a patient 103 based on the customizations made by the care provider 101. In doing so, the care plan management application 111 identifies conflicting tasks across the selected care protocol templates 114. For example, a care protocol for high blood pressure may include a task instructing a patient to take 85 milligrams of aspirin three times a day, while another care protocol for a sprained ankle includes a task instructing the patient to take 100 milligrams of aspirin three times a day.

Generally, the patient information 113 represents patient-specific information describing a patient's medical history and treatment history. In one embodiment, the care plan management application 111 may generate the care plan 115 based on the patient information 113, in addition to customizations to care protocol templates 114 that the care provider 101 provides. Patient information 113 may include medications previously prescribed to the patient 103 and whether the medications had a beneficial or adverse effect towards the patient. In a case where a particular medication has had an adverse effect towards a patient 103, the care plan management application 111 may flag tasks associated with taking the medication to the care provider 101 configuring the care plan 115. In response, the care provider 101 may edit or remove the task.

Once generated, the care plan management application 111 may store the care plan 115 on the care platform server 110. Further, the care plan management application 110 transmits the care plan 115 to a mobile device 135 (e.g., to a patient care application 136 executing on the mobile device 135) of the patient 103. Information dialogs related to the care plan (shown as care plan 137) can be provided to the patient 103 through input/output devices of the mobile device. For example, the patient care application 136 could generate a graphical user interface including the information dialogs and could present the graphical user interface to the patient via a display device of the mobile device 135. As another example, the patient care application 136 could output an educational video detailing how to properly perform a particular exercise prescribed for the patient 103 as part of the care plan 137, using the display device and one or more speaker devices of the mobile device 135. Of note, although the present examples are described with respect to mobile device 135, such examples are without limitation and are provided for illustrative purposes only. More generally, any suitable devices can be used (e.g., a home computer, a smartTV, etc.), consistent with the functionality described herein.

Moreover, the mobile device 135, upon receiving the care plan, could configure one or more monitoring devices to monitor one or more patient metrics as specified by the care plan. For example, the mobile device 135 could configure logic on a heart rate monitor device worn by the patient to monitor the patient's heart rate and to detect when the patient's heart rate exceeds a threshold number of beats per minute specified within the care plan. The heart rate monitor device, upon detecting that the threshold condition has been satisfied, could transmit an alert to the mobile device 135, which could in turn perform an action as specified by the care plan. For example, the mobile device 135, upon receiving the alert, could display a notification to the patient, informing the patient that his heart rate is elevated and instructing the patient to sit down and rest for a period of time. As another example, the mobile device 135 could generate a notification to the care plan management application 111, informing the care plan management application 111 that the patient's heart rate exceeds the threshold amount of beats per minute. Doing so allows for patient events to be detected immediately by the corresponding monitoring device 140, rather than waiting on the care plan management application 111 to parse through the log of data collected from the various sensor devices 140.

The patient care application 136 may display information related to the care plan 137, such as phases, tasks, and other information about conditions targeted for treatment by the care plan 137. When the patient 103 performs a task, the patient 103 records progress in the patient care application 136. The patient care application 136 relays this information to the care plan management application 111. Doing so allows the care provider 101 to monitor the body metrics of the patient 103 and adherence to the care plan. Further, depending on how the patient 103 responds to the care plan 137, the care plan management application 111 may adjust certain tasks. For example, the patient 103 could be assigned the task of reading particular educational content every morning as part of the administration of the care plan 137. If the care plan management application 111 then detects that the patient 103 is infrequently completing the assigned task, the care plan management application 111 could alter the care plan 137 to provide the educational content through a different medium. For instance, the care plan management application 111 could alter the care plan 137 such that the patient is assigned to watch an educational video on the same topic as the written educational content, using the mobile device 135 once per week. Doing so allows the care plan 137 to be adjusted to suit the individual preferences of the patient 103, while helping to ensure that the patient 103 completes the assigned tasks laid out in the care plan 137.

In one embodiment, sensor devices 140 may interact with the patient care application 136 and assist the patient 103 in reporting body-related metrics to the care platform server 110. As shown, such sensor devices 140 may include a body sensor 141, a weighing scale 142, and a blood pressure cuff 143. Each of the sensor devices 140 may capture different body metrics of the patient 103. For example, when applied to the body of patient 103, the body sensor 141 captures biometric data (e.g., heart rate, electrocardiogram (ECG) data, etc.) in real-time. In addition, each of the sensor devices 140 may be configured to transmit the body-related metrics electronically to the patient care application 136 on the mobile device 135. In turn, the patient care application 136 sends the captured metrics to the care plan management application 111.

In one embodiment, the sensor devices 140, upon detecting an observation threshold has been reached, are configured to perform an initial classification of the event. In a particular embodiment, the mobile device 135 is configured to perform the initial classification of the event, based on the care plan 137. For example, the body sensor 141, upon detecting that the ECG data collected from the patient 103 indicates an erratic heart behavior, could classify the event as a cardiac event. This initial classification, along with the relevant ECG data (e.g., ECG data a predetermined length of time before and after the event), could be transmitted to the mobile device 135 (e.g., over a Bluetooth® communications link) and the patient care application 136 could then forward the event data on to the care plan management application 111 over the network 145 (e.g., the Internet). Upon receiving the event data, the care plan management application 111 could detect that the event was initially classified as a cardiac event and could perform a more detailed analysis of the event data to more accurately classify the event. For example, the care plan management application 111 could be configured recognize a number of sub-classifications of cardiac events and could analyze the received event to determine which of the sub-classifications best matches the event data. The care plan management application 111 could then record the determined sub-classification. In some situations, the care plan 115 for the patient 103 could specify a particular treatment plan to perform upon determining a particular sub-classification of event. In such a situation, the care plan management application 111 could transmit a request to the patient care application 136 to initiate the treatment plan on the mobile device 135. Doing so allows for a more computationally expensive analysis of the event data to be performed using the computing resources of the care provider environment 105, rather than the limited resources of the sensor devices 140 or the mobile device 135, while quickly determining an initial classification for the event using the sensor devices 140.

In one embodiment, the care plan management application 111 is configured to provide feedback to the patient 103 and to adjust the provided feedback over time based on the patient's behavior and preference. For example, an exemplary care plan 115 could prescribe continuing education activities related to the patient's condition and the initial care plan 115 could specify that the patient is to read a weekly article on an aspect of the patient's condition each week. The care plan management application 111 could then monitor the patient's adherence to the assigned task of reading continuing education articles according to the prescribed schedule. For example, if the care plan management application 111 accesses the articles using the mobile device, the care plan management application 111 could record each time the patient accesses the articles and when the patient does not review a particular week's article. As another example, in an embodiment where the patient reviews the articles using a device other than the mobile device 135, the patient care application 136 could provide an interface through which the patient can provide input specifying that the patient has reviewed the week's article and the care plan management application 111 could detect weeks when no input is received, thus indicating that the patient did not review that week's article.

The care plan management application 111 could continue to monitor the patient's adherence to the assigned task and, upon determining that the patient's adherence is sufficiently low (e.g., below a threshold amount of adherence), the care plan management application 111 could alter the patient's care plan in an attempt to boost the patient's adherence to the assigned task. For instance, the care plan management application 111 could alter the schedule at which the prescribed tasks are to be performed, e.g., altering the day of the week on which the task is to be performed, altering the duration of the task, increasing the window of time during which the patient can complete the task and be considered on time, and so on.

In one embodiment, the care plan management application 111 is configured to adjust the assigned task based on the patient's level of adherence to the assigned task. For instance, if the care plan management application 111 detects that the patient is poorly adhering to the assigned task of reading a weekly continuing educational article related to a condition the patient is diagnosed with, the care plan management application 111 could alter the patient's care plan to assign a different task to the patient to attempt to improve the patient's adherence. For example, the care plan management application 111 could remove the task of reading a weekly article from the patient's care plan and could replace the task with a new task of watching a weekly educational video on an aspect of the diagnosed condition, e.g., using the mobile device. The care plan management application 111 could continue monitoring the patient's adherence to the newly assigned task and could make further changes to the patient's care plan in the event the patient's adherence continues to suffer.

In determining how to modify the assigned task, the care plan management application 111 can consider historical patient information for the patient. For example, continuing the above example, the care plan management application 111 could replace the assigned task of reading an educational article with the task of watching a weekly video, and the care plan management application 111 could then determine that the patient's level of adherence to the assigned task significantly increased. The care plan management application 111 could then save patient data indicating the alteration made to the care plan and that the alteration resulted in a positive effect on the patient's level of adherence. In subsequently modifying other aspects of the patient's care plan, the care plan management application 111 could access this patient data and could determine that the patient appears to adhere more closely to assigned tasks involving video media than tasks involving textual materials. Accordingly, the care plan management application 111 could give a preference to assigned tasks involving video content in modifying the patient's care plan. Doing so provides an individually tailored care plan that is dynamically adjusted based on the patient's individual preferences.

Figure 2:
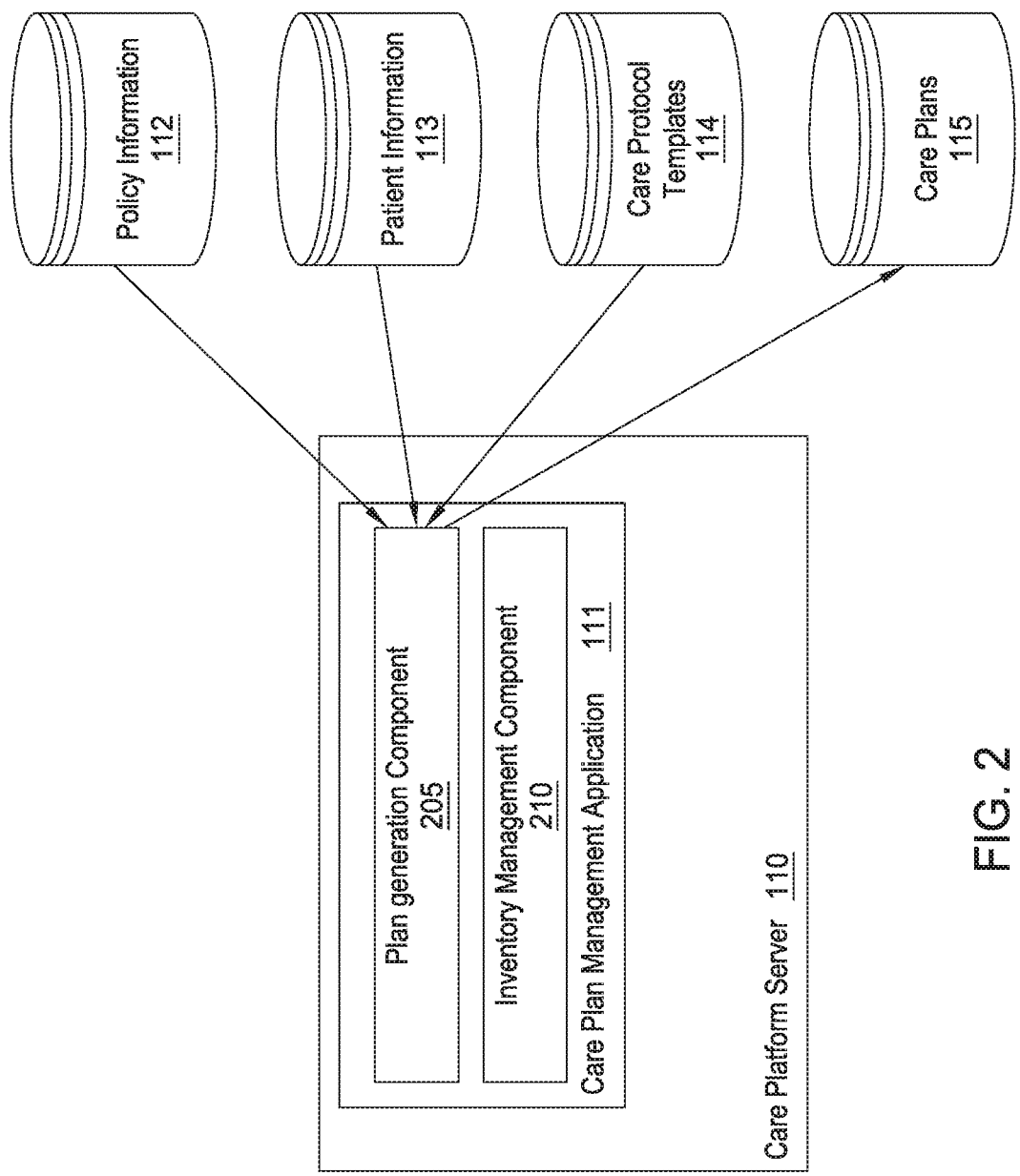
FIG. 2 further illustrates the care platform server described in FIG. 1, according to one embodiment.

FIG. 2 further illustrates the care platform server 115, according to one embodiment. As stated, the care plan management application 111 can be configured to generate a care plan 115 based on care protocol templates 114 selected by a care provider 101 and also based on policy information 112 and patient information 113.

As shown, the care plan management application 111 further includes a plan generation component 205 and an inventory management component 210. The plan generation component 205 receives selections of care protocol templates 114 from a care provider 101. The plan generation component may populate a care plan 115 with the phases, tasks, and thresholds specified in each of the care protocol templates 114 selected by the care provider 101.

Further, the plan generation component 205 may receive customizations to the tasks and thresholds of the care protocol templates 114. In addition, the care provider 101 may insert tasks and thresholds to any of the care protocol templates 114. The plan generation component 205 generates the care plan 115 based on the care protocol templates 114 and the care plans 115. In doing so, the plan generation component 205 ensures that any customizations to the care protocol templates 114 made by the care provider 101 comply with policy information 112.

Further, the plan generation component 205 can resolve task and threshold information that conflict between different care protocol templates. In one embodiment, tasks and thresholds may be associated with conflict resolution rules such that in the event a conflict arises, the plan generation component 205 may resolve the conflicting tasks and thresholds based on such properties. The properties may be configured by care providers 103. For example, assume that a care protocol template 114 for a sprained ankle condition includes a task instructing a patient to take 80 milligrams of aspirin in the morning. Assume also that a care protocol template 114 for hypertension includes a task instructing a patient to take 150 milligrams of aspirin in the morning. A conflict resolution rule for the task of taking aspirin in the morning may specify that in the event of a conflict, the task instructing the patient to take the higher dosage should override. Thus, when a care provider 103 selects the care protocol templates 114 for a sprained ankle and hypertension for a patient, the plan generation component 114 reconciles the conflicting tasks by inserting the 150 milligrams of aspirin step in the care plan and disregarding the 80 milligrams of aspirin step. Another example of a conflict that may arise includes different care protocols instructing a patient to take two types of medication that should not be taken together. Conflict resolution rules for such tasks may include logic to avoid such combinations or raise a flag to the care provider 103 selecting the protocols. The care provider 103 may further customize the care protocol templates 114 in response.

In one embodiment, the plan generation component 205 may make additional customizations based on patient information 113. As stated, patient information 113 may include patient medical histories. Such histories may contain past treatment information for a given patient as well as information on the effectiveness of certain treatments to the patient. The patient information 113 may include other data such as allergies, past afflictions, etc. The plan generation component 205 may adjust tasks based on the patient information 113. For example, if the patient information 113 indicates that a patient is allergic to ibuprofen, the plan generation component 205 may substitute tasks mentioning ibuprofen with a similar medication. Alternatively, the plan generation component 205 may flag the task for further review by the care provider 101.

The inventory management component 210 maintains a store of sensor device configurations for patients registered with the care environment. The inventory management component 210 associates the patient care application 136 with the sensor devices 140. Further, the inventory management component 210 also associates a generated care plan with the patient care application 136 and sensor devices 140. Doing so ensures that the plan generation component 205 sends a generated care plan to the correct mobile device as well as configures the patient care application 136 and sensor devices 140 of the patient 103 with the relevant threshold information. Once configured, the patient care application 136 allows the patient 103 to begin adhering to the individualized care plan.

Figure 3:
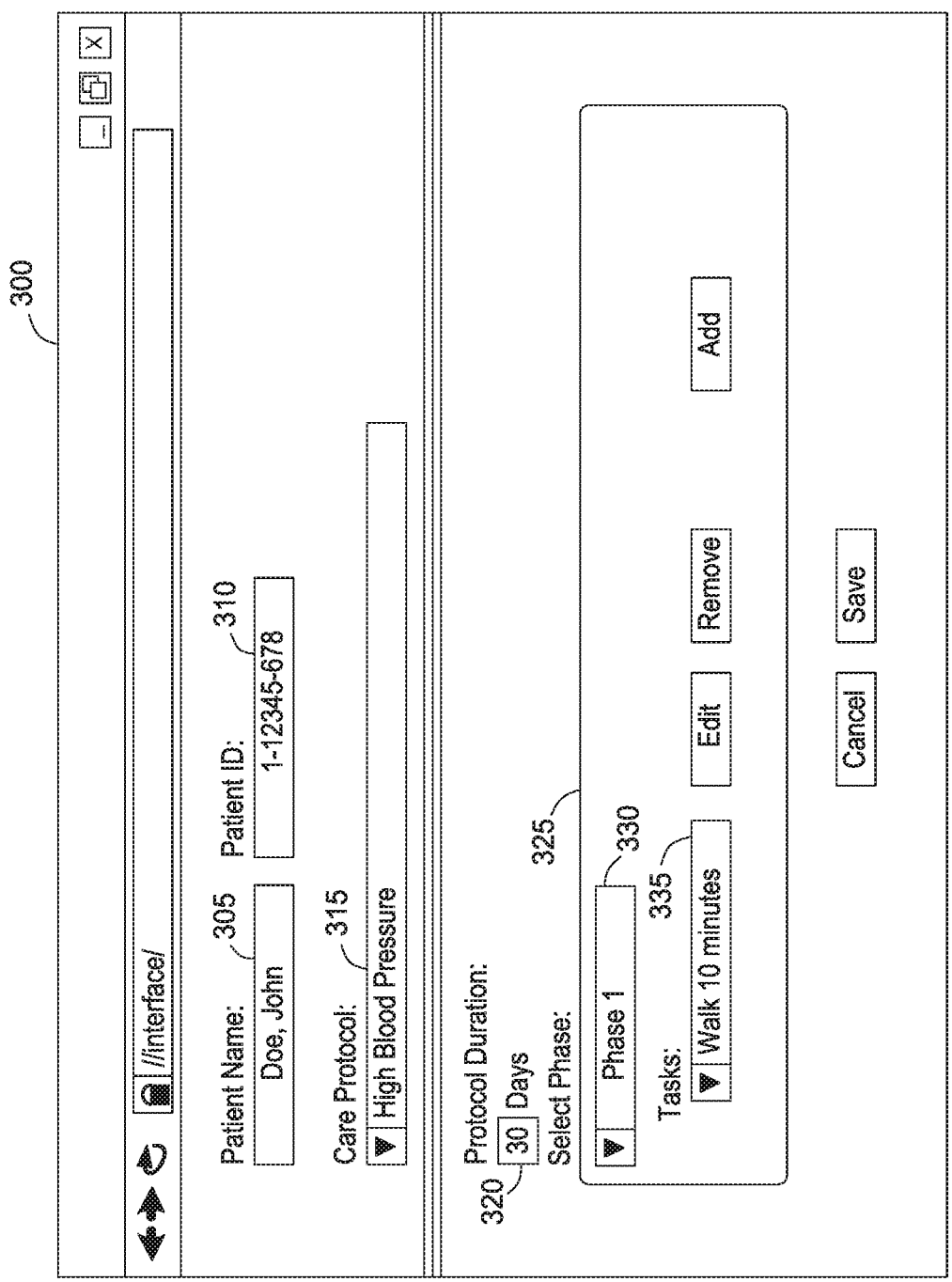
FIG. 3 illustrates an example care protocol template, according to one embodiment.

FIG. 3 illustrates an example care protocol template 300, according to one embodiment. In one embodiment, the care protocol template 300 may be presented to a care provider 101 via a web browser interface. For example, the care provider 101 may access a portal server that presents the interface to the care provider 101. After entering a request to create a care plan, the interface may present the template 300 to the care provider 101. The care provider 101 customizes saves enters information into and modifies each template 300. After doing so, the plan generation component 205 may create the care plan based on the templates and customizations.

As shown, the template 300 includes fields 305 and 310, where the care provider 101 may enter a name and an identifier of a patient to associate with a care plan. In addition, the template 300 includes a drop down menu 315 that allows the care provider 101 to select a particular care protocol. The drop down menu 315 may include a list of conditions for which a care protocol exists in the care platform server. In this case, the care protocol shown is for high blood pressure.

After selecting a care protocol via the drop down menu 315, the interface may present tasks, thresholds, and metrics associated with the care protocol. For instance, the bottom half of the template 300 shows phase and task information associated with the care protocol for high blood pressure. The care provider 101 may modify a variety of tasks and other information associated with the care protocol. For example, the template 300 includes a field 320 that allows the care provider 101 to specify a duration for the care protocol to last.

In addition, the template 300 allows the care provider 101 to view phase information 325 associated with the protocol. The care provider 101 may select a phase to view using a drop down menu 330. After selecting a phase, the care provider 101 may view tasks associated with a particular phase, e.g., via a drop down menu 335. The template 300 may allow the care provider 101 to edit or remove selected tasks. The care provider 101 may also add tasks for phases as well.

Once the care provider 101 is finished customizing the selection, the care provider 101 may save the customizations. The plan management component 205 may allow the care provider 101 to add other care plan protocols until the care provider 101 has selected all the needed protocols for a patient.

FIG. 4 illustrates a task view 400 of the care protocol template 300, according to one embodiment. The task view 400 provides additional metrics that a care provider 101 may evaluate and edit for a given care protocol when creating a care plan to assign to a patient. As shown, the task view 400 includes fields 405, 410, and 415 that indicate a patient name, a patient ID, and a care protocol condition. The bottom half of task view 400 lists tasks and thresholds associated with the selected care protocol. In this case, the tasks are associated with a "high blood pressure" care protocol.

As shown, the task view 400 lists the tasks in a column 420. Each task in the list 420 specifies an instruction that a patient should take, e.g., wearing a body sensor, taking blood pressure, and taking 60 milligrams of aspirin. Further, the task view 400 provides a column 425 specifying a frequency at which to perform a corresponding task, e.g., taking 60 milligrams of aspirin every morning.

The task view 400 also lists observation threshold sets 430 that a care provider 101 may configure. Each threshold set may correspond to a particular task metric in a care protocol, e.g., that is monitored though a sensor device associated with a patient. As shown, each threshold set 1 includes columns associated with a threshold type, a value, a warning level, associated symptoms reported by a patient (e.g., via the patient care application 136), and alert type. Each threshold is associated with a tier-based warning level that indicates a severity of the threshold. For example, a tier 1 warning level may be of a mild severity, while in contrast, a tier 3 warning level may be of a high severity. If a patient reaches a particular observation threshold, the care platform server may take a specified action, such as recording the event to a medical chart of a patient, notifying a care provider 101, etc. The care plan management application 111 may also prompt the patient 103 to report any symptoms (e.g., via the patient care application 136). Based on rules associated with the threshold triggers, the care plan management application 111 may elevate the warning level to the next tier in response to reported symptoms being noted with the observed metrics. For example, if the care plan management application 111 detects, based on a specified threshold, that the heart rate of the patient is over a value X, the care plan management application 111 may instruct the patient to rest and also prompt the patient to enter symptoms. If particular symptoms (specified in the threshold) are present, the care plan management application 111 may elevate to the next tier in response. However, if no (or other) symptoms are present, then the care plan management application 111 may continuously monitor the heart rate of the patient for a given time period to determine whether the heart rate drops within an acceptable range, and act accordingly after the end of the time period.

Consider threshold set 1 shown in the task view 400. Threshold set 1 corresponds to thresholds related to monitoring weight over a weekly basis. If the care platform server detects that a patient associated with the care plan has gained 2.5 kilograms over a weeklong period, the care platform server may record the information on the patient's medical chart. A care provider 101 may add, delete, or modify observation thresholds as necessary. Further, the care provider 101 may add or delete threshold sets for associated tasks, as well.

Figure 5:
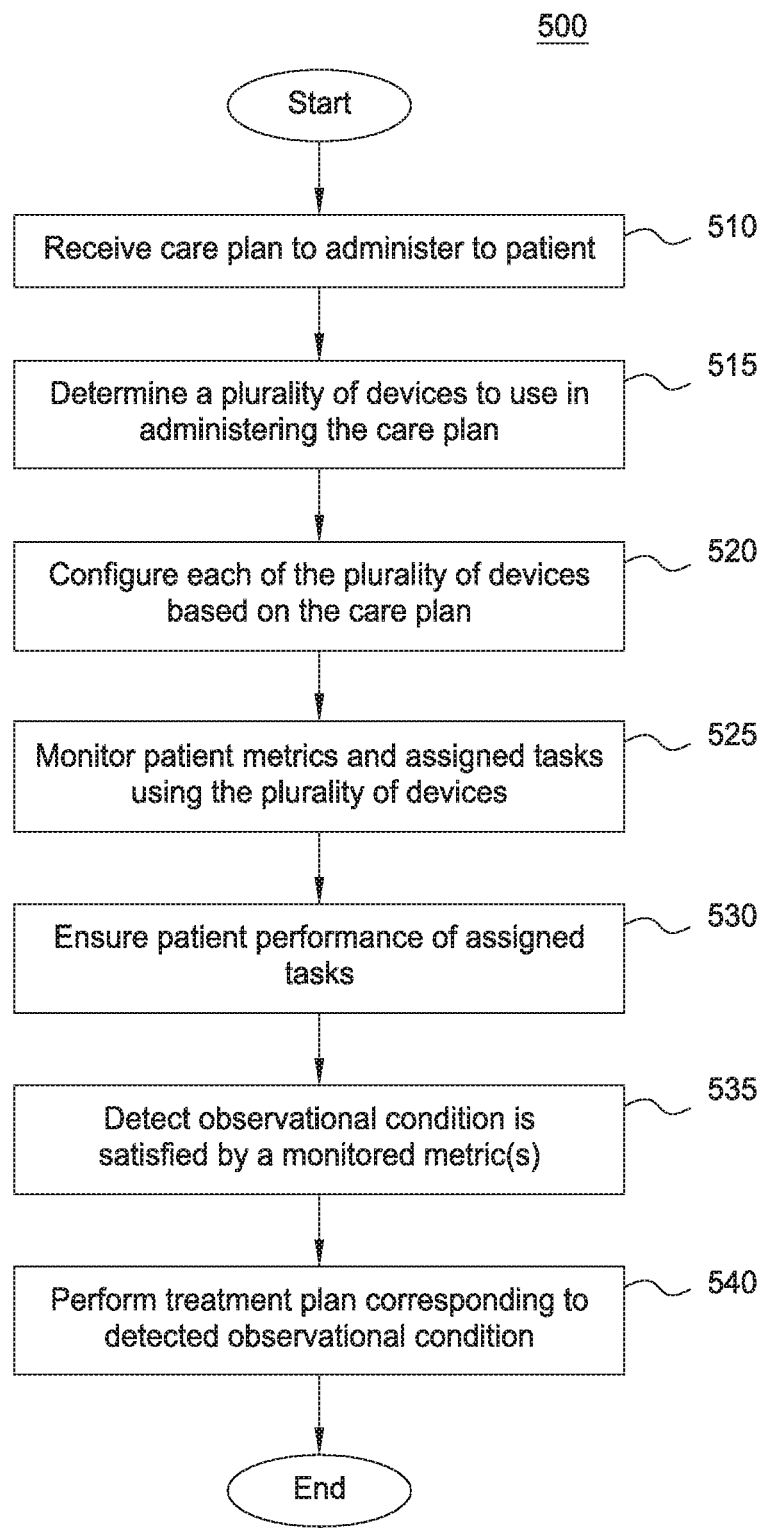
FIG. 5 is a flow diagram illustrating a method of administering a care plan to a patient, according to one embodiment.

FIG. 5 is a flow diagram illustrating a method of administering a care plan to a patient, according to one embodiment. As shown, the method 500 begins at block 510, where the care plan management application 111 receives a care plan to administer to a patient. For example, such a care plan could have been created by a health care provider using the interface depicted above in FIGS. 3 and 4. Moreover, as discussed above, the care plan could specify assigned tasks for the patient to perform, a number of observational metrics to monitor, observational thresholds that, when met by the collected observational metric data, signify the occurrence of an event, and treatment plans specifying a treatment protocol for responding to the occurrence of such an event.

Upon receiving the care plan, the care plan management application 111 determines a plurality of devices to use in administering the care plan (block 515). In one embodiment, the care plan management application 111 first determines whether the patient already owns any monitoring devices that the patient would like to use as part of the administration of the care plan. For example, the patient could already have purchased a bathroom scale capable of measuring the patient's body weight and transmitting the weight data over a communications network (e.g., a Bluetooth® communications link, an IEEE 802.11 wireless network connection, etc.). In such a situation, the care plan management application 111 could give a preference to the devices the patient already owns to avoid redundancy amongst the monitoring devices and to reduce the cost of administering the care plan. Additionally, in some situations, multiple available devices may be capable of collecting one of the observational metrics specified in the care plan (e.g., ECG heart beat data). In such an example, the health care provider (e.g., a physician) could select one of the multiple devices to use.

Once the devices are determined, the care plan management application 111 configures each of the devices based on the care plan (block 520). For instance, the care plan management application 111 could configure each of the devices to monitor a respective one or more of the observational metrics specified by the care plan. As an example, a bathroom scale device could be assigned to collect data regarding the patient's weight, while a body-worn monitoring device could be assigned to collect ECG heart beat data, breathing data and blood pressure data. Additionally, some or all of the devices could be configured with threshold information that, if met or exceeded by the collected observational metric data, signifies the occurrence of an event.

The care plan management application 111 then monitors the observation metrics of the patient and the patient's adherence to the assigned tasks using the monitoring devices (block 525). For instance, the body-worn monitoring device could be configured to detect when the ECG heart beat data becomes sufficiently erratic to satisfy a particular threshold and to generate a cardiac event in response. The monitoring device could then transmit the cardiac event data to the patient care application 136 on the mobile device 135, which could in turn forward the event data on to the care plan management application 111 for storage and further analysis.

The care plan management application 111 also ensures patient performance of the assigned tasks specified in the care plan (block 530). As an example, a mobile device could be configured to generate a graphical user interface that allows the patient to input when the patient has completed a particular assigned task. Upon detecting that a patient has not completed an assignment task within a window of time specified in the care plan, the patient care application 136 on the mobile device 135 could generate a reminder for the patient (e.g., displaying a graphical message reminding the patient of the assigned task along with playing a notification sound signifying a new message has been received).

In one embodiment, the care plan management application 111 is configured to adjust the assigned tasks based on the patient's history of compliance. For instance, a patient could be assigned the task of reading an educational article on an aspect of the patient's diagnosed condition every, but the care plan management application 111 could determine that the patient's compliance with the assigned task is very poor (e.g., 25% compliance). Based on such a determination, the care plan management application 111 could alter the assigned task to use another form of media content that the patient may prefer more than the written articles. For example, the care plan management application 111 could alter the care plan to assign the patient the task of watching an education video on an aspect of the patient's condition on a daily basis, rather than reading the educational article. Moreover, if the care plan management application 111 determines that such an alteration improves the patient's compliance with the assigned task, the care plan management application 111 could record this information for use in assigning future tasks to the patient. For example, the care plan management application 111 could determine that this particular patient tends to prefer video content over textual content, and thus could assign a preference to tasks involving video content in the future.

In administering the care plan, the care plan management application 111 detects that an observational condition is satisfied by a monitor metric(s) (block 535) and, in response, initiate the performance of a treatment plan corresponding to the detected condition (block 540), at which point the method 500 ends. Generally, the treatment plan represents a set of actions that can be performed as part of the diagnosis and treatment of the detected event, and may further specify conditional logic indicating if and when each action within the treatment plan should be performed.

Figure 6:
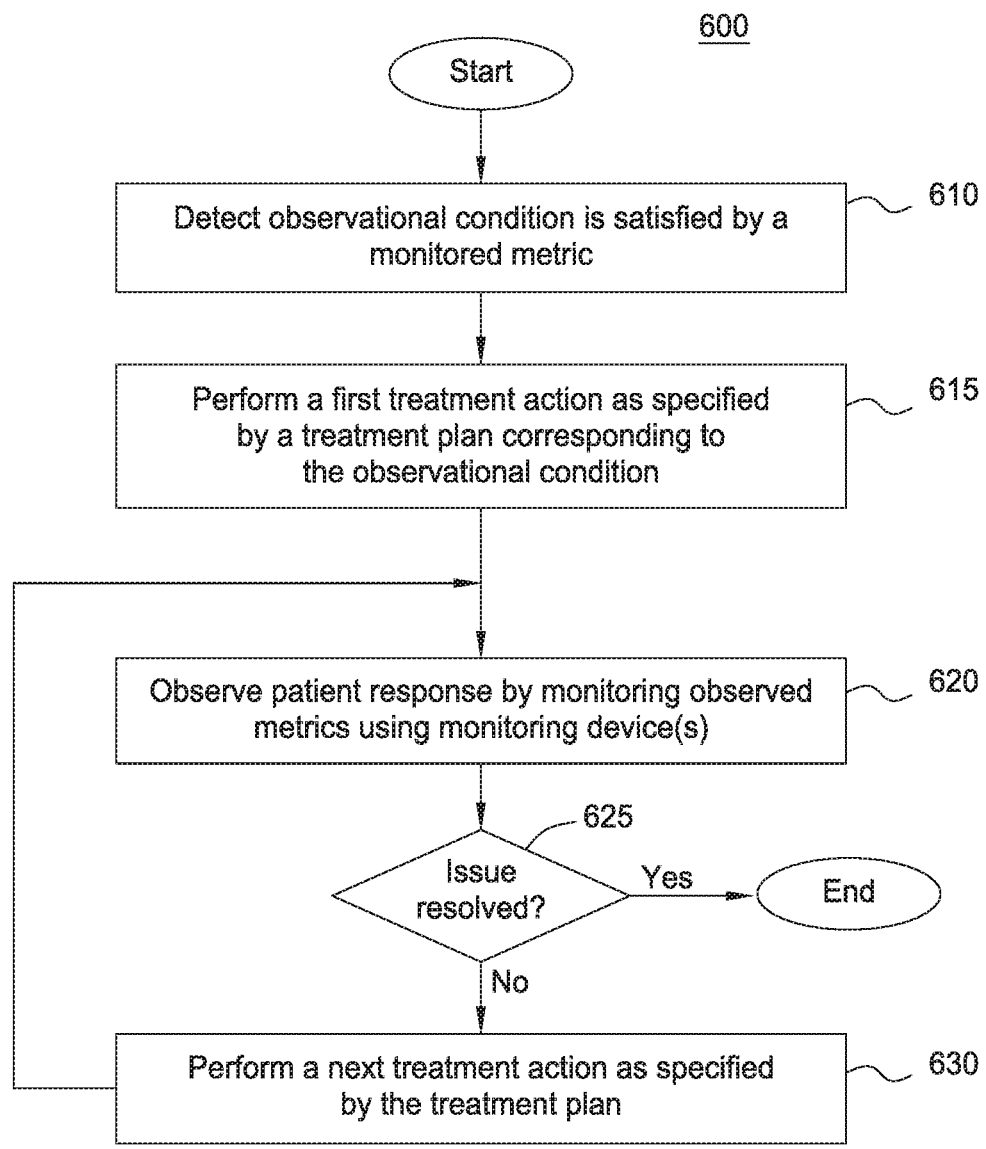
FIG. 6 is a flow diagram illustrating a method of administering treatment as part of a care plan, according to one embodiment.

FIG. 6 is a flow diagram illustrating a method of administering treatment as part of a care plan, according to one embodiment. As shown, the method 600 begins at block 610, where the care plan management application 111 detects that an observational condition is satisfied by a monitor metric. For instance, an elevated heart rate event could occur when a patient's heart rate relative to a measure of the patient's current activity level exceeds a threshold value. Here, by accounting for the patient's activity level, embodiments can avoid false positive events caused by the patient's exercise routine (i.e., or other activities during which an elevated heart rate would be expected).

The care plan management application 111 then performs a first treatment action as specified by the treatment plan corresponding to the observed condition (block 615). For example, a treatment plan for an elevated heart rate event could first request that the patient sit down and rest. The care plan management application 111 could then observe the patient's response by continuing to monitor the patient's heart beat and heart rate using the monitoring devices (block 620). If the issue has been resolved after some specified or predetermined period of time (block 625), the method 600 ends. In such an event, the care plan management application 111 could log the occurrence of the event and the event data surrounding the occurrence of the event (e.g., collected data from a predetermined period of time before and after the event) for subsequent review by a health care professional.

If the issue is not resolved, the care plan management application 111 performs a next treatment action as specified by the treatment plan (block 630), and the method 600 returns to block 620, where the care plan management application 111 again observes the patient's response to the treatment action. This behavior continues until the issue is resolved, either by the patient's biometric data returning to the expected range or when the issue is escalated to a health care professional.

Figure 7:
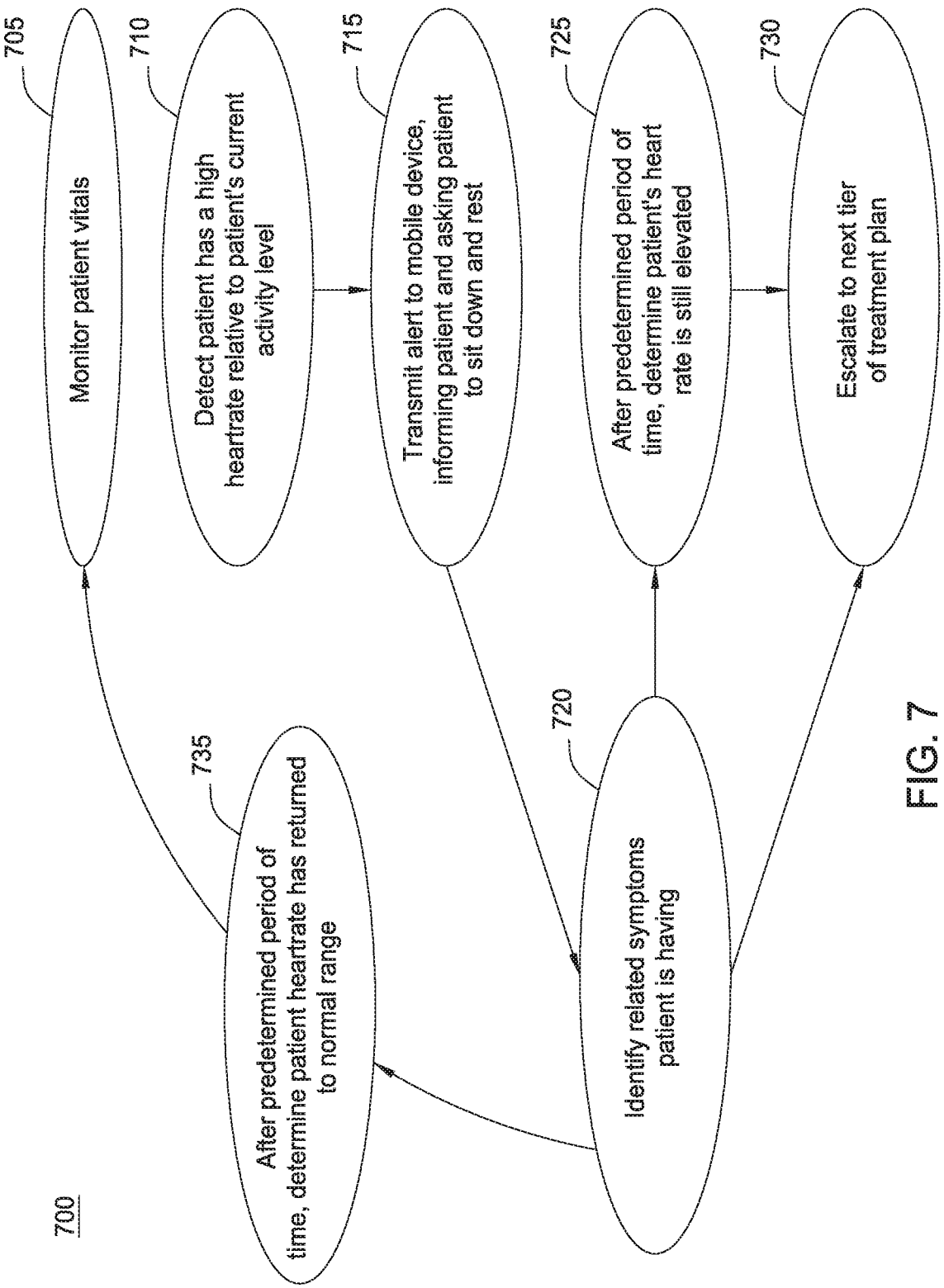
FIG. 7 is a flow diagram illustrating a treatment plan workflow within a care plan, according to one embodiment.

FIG. 7 is a flow diagram illustrating a treatment plan, according to one embodiment. As shown, the treatment plan 700 begins at block 710, where the care plan management application 111 detects a patient currently has a high heart rate relative to the patient's activity level. In the depicted treatment plan 700, the care plan management application 111 then transmits an alert to the patient care application 136 on the mobile device 135, to inform the patient of the event that is occurring (i.e., that the patient's heart rate is currently and unexpectedly elevated) and requesting the patient sit down and rest (block 715).

Additionally, the care plan management application 111 identifies any symptoms the patient is currently experiencing (block 720). For instance, the patient care application 136 on the mobile device 135 could output an interface requesting that the patient enter any symptoms he is currently experiencing. As an example, the interface could specify a number of symptoms commonly experienced along with an elevated heart rate and the patient could select symptoms he is currently experiencing using a touchscreen display of the mobile device 135. The treatment plan could further include logic that specifies how to respond to various combinations of symptoms and observational data.

In considering the patient's symptom(s), the care plan management application 111 can also consider whether the symptom(s) occurred within a relevant time window. In other words, the care plan can designate the temporal relationship that must exist between each detected event and reported symptoms, in order for the symptoms to be considered relevant to the event. For example, for every event and threshold, the care plan could specify a range as to when the relevant symptom(s) must occur in order to be considered applicable to the event. For example, for an event having a threshold set to detect when the patient has gained weight since a previous moment in time, the event could further specify that the symptom of a bloated feeling occurring within a 2 day window around the date of the detected weight gain is considered relevant to the weight gain event. As another example, for an arrhythmia event, the care plan could specify that the symptom of palpitations must occur within a 15 minute window around the arrhythmia event in order to be considered applicable to the event.

If the care plan management application 111 determines that the patient's symptoms (if any) are not indicative of an event requiring immediate medical attention, the care plan management application 111 reassesses the patient's condition after a predetermined period of time (e.g., 15 minutes) to determine whether the patient's heart rate has returned to the normal range or is still elevated (block 725). If at this point the care plan management application 111 determines the patient's heart rate is still outside of the normal range, the care plan management application 111 escalates the treatment to a next tier of the treatment plan. For instance, such escalated treatment may include generating and transmitting an alert to medical personnel, informing them of the patient's current condition.

Moreover, in the depicted treatment plan 700, the care plan management application 111 can also determine based on the patient's current symptoms that the treatment should immediately be escalated to the next tier of the treatment plan and could immediately alert medical personnel of the patient's condition. As another example, if the patient indicates that he is currently experiencing the symptoms of dizziness, nausea, and sweating, the care plan management application 111 could again determine that a potentially significant cardiac event is occurring and may once again escalate the treatment. On the other hand, if after 15 minutes of resting the patient's heart rate has dropped into an expected range of beats per minute, the care plan management application 111 could determine that no further action is needed at this time and could simply log the occurrence of the event and along with the event data corresponding to the event (e.g., ECG data before and after the detected event).

On the other hand, if the care plan management application 111 assesses the patient's symptoms and determines that the symptoms (if any) are not indicative of an event requiring mediate medical attention, and if the care plan management application 111 further determines that after a predetermined period of time the patient's heart rate has returned to the normal range (block 735), then the care plan management application 111 treatment can deescalate and the care plan management application 111 can return to block 705, where the care plan management application 111 continues monitoring the patient's vitals to detect any subsequent occurrences of events.

Figure 8:
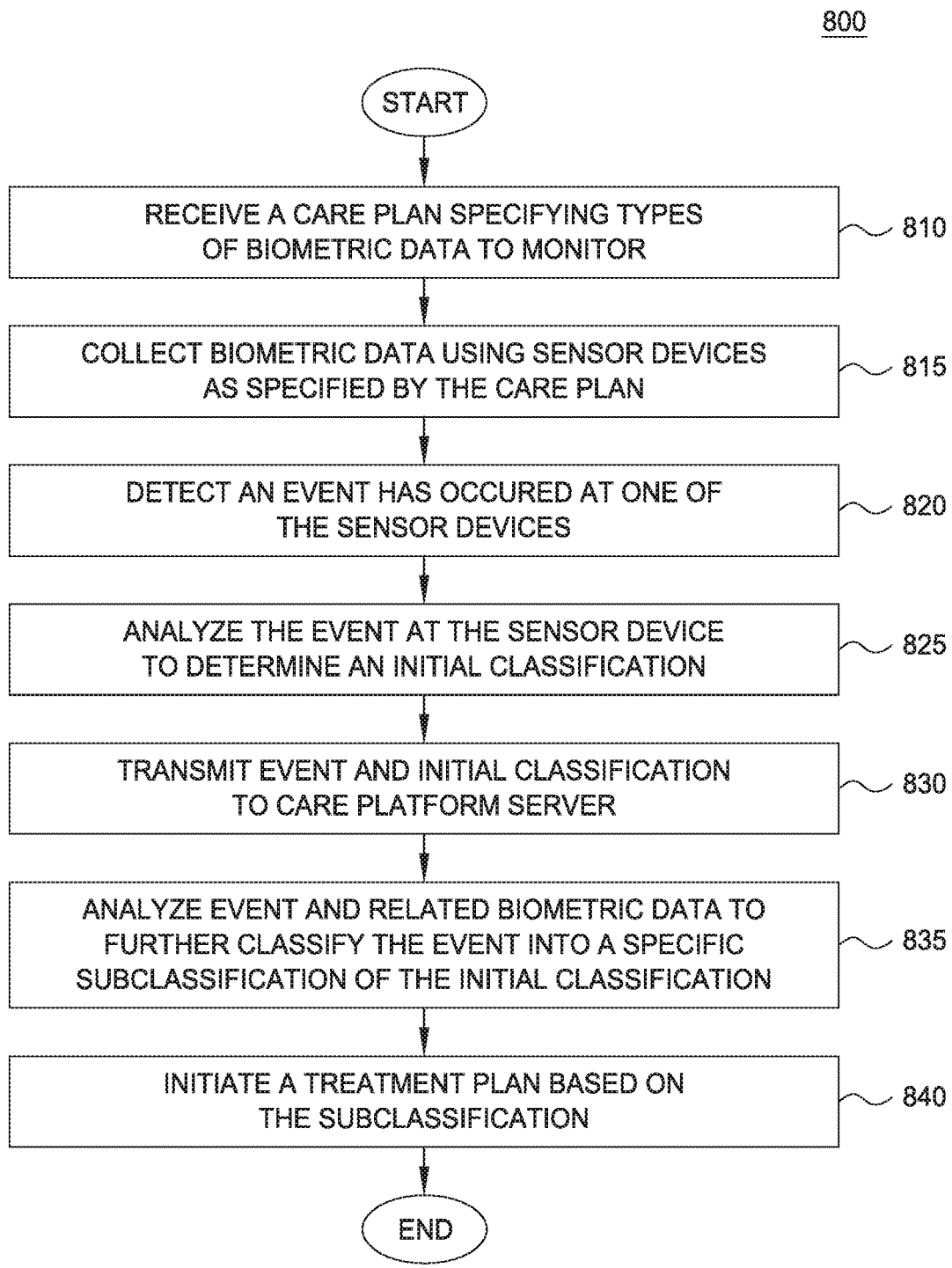
FIG. 8 is a flow diagram illustrating a method of administering a care plan, according to one embodiment.

FIG. 8 is a flow diagram illustrating a method of administering a care plan, according to one embodiment. As shown, the method 800 begins at block 810, where the patient care application 136 on the mobile device 135 receives a care plan specifying one or more types of biometric data to monitor for a particular patient. For instance, the care plan could be created by the patient's healthcare provider (e.g., a physician) based on the care protocol templates 114. Upon receiving the care plan, the patient care application 136 configures each sensor device 140 to monitor a respective type(s) of biometric data specified in the care plan. The patient care application 136 can further configure the sensor devices 140 with pattern information for use in detecting occurrences of health-related events. For example, a body-worn ECG device 141 could be configured to recognize particular patterns of ECG data indicative of cardiac events.

The sensor devices 140 then collect the biometric data as specified by the care plan (block 815). Generally, the collected biometric data is transmitted from the sensor devices 140 to the care plan management application 111 in the care provider environment 105 for further analysis. In one embodiment, the sensor devices 140 are configured to transmit the collected biometric data to the mobile device 135 (e.g., using wireless communications such as Bluetooth® communications) and the patient care application 136 on the mobile device is configured to forward the biometric data on to the care plan management application 111 via a network connection (e.g., a Transmission Control Protocol/Internet Protocol (TCP/IP) socket connection across the Internet). In a particular embodiment, at least one of the sensor devices 140 is configured to transmit the collected biometric data directly to the care plan management application 111 via the network 145. In another embodiment, one of the sensor devices 140 is configured to transmit the collected biometric data to another entity (e.g., a service hosted by a manufacturer of the bodyweight scale 142), which in turn provides an application programming interface (API) through which the biometric data can be passed to the care plan management application 111. More generally, any technique suitable for transmitting the collected biometric data from the sensor devices 140 to the care plan management application 111 can be used.

At some point during the biometric data collection, one of the sensor devices detects that a health-related event has occurred based on the collected data (block 820). The sensor devices further analyzes the biometric data for the event to determine an initial classification for the event (block 825). For example, the sensor device could be preprogrammed to recognize one or more patterns of biometric data indicative of an occurrence of the health-related event, and upon detecting a portion of the collected biometric data matches one of the preprogrammed patterns, the sensor devices could detect that the event has occurred and could classify the event with an initial classification based on the matching pattern. For example, the sensor device could be configured with various patterns of biometric data, each corresponding to either a cardiac event or a diabetic event. Upon determining that a portion of the collected biometric data matches a pattern corresponding to a cardiac event, the sensor devices could initially classify the portion of biometric data as an occurrence of a cardiac event.

In one embodiment, the sensor devices are configured to directly relay the biometric data to the mobile device 135. In such an embodiment, the mobile device 135 may be configured with logic for detecting that an event has occurred when a portion of the biometric data matches a preconfigured pattern and for analyzing the biometric data to determine an initial classification of the event. Such an embodiment may be advantageous, for example, when the sensor devices 140 are incapable of or ill-suited for performing the event detection and analysis processing.

The sensor device then transmits the event and the initial classification to the care platform server (block 830). As discussed above, the sensor device can transmit the event data in a variety of ways, with examples including (without limitation) via the mobile device 135, directly using a network connection over network 145, indirectly via a manufacturer site that in turn provides the data to the care platform server, and so on. Upon receiving the event data, the care plan management application 111 analyzes the event and the related biometric data to further classify the event into a specific sub-classification of the initial classification. For example, while the sensor device may have initially classified the event as a generic cardiac event, the care plan management application 111 could analyze the biometric data to determine a specific sub-classification of cardiac event that the patient experienced. Doing so allows for an initial classification of the event to be quickly determined at the sensor-device level, without requiring the sensor device to have the processing resources to perform a more in-depth analysis of the collected biometric data.

Once the sub-classification of the event is determined, the care plan management application 111 initiates a treatment plan based on the determined sub-classification (block 840), and the method 800 ends. For example, upon determining that a particular type of cardiac event has occurred, the care plan management application 111 could transmit instructions to the patient care application 136 for display on the mobile device 135, instructing the patient to sit down and perform breathing exercises in an attempt to reduce the patient's current heart rate. As another example, the treatment plan may simply specify to log the event for subsequent review by the patient's care provider 101. As yet another example, in the case of an occurrence of a more urgent event, the care plan management application 111 could alert emergency personnel as to the occurrence of the event and could provide the patient's contact information to the emergency personnel as needed.

Figure 9:
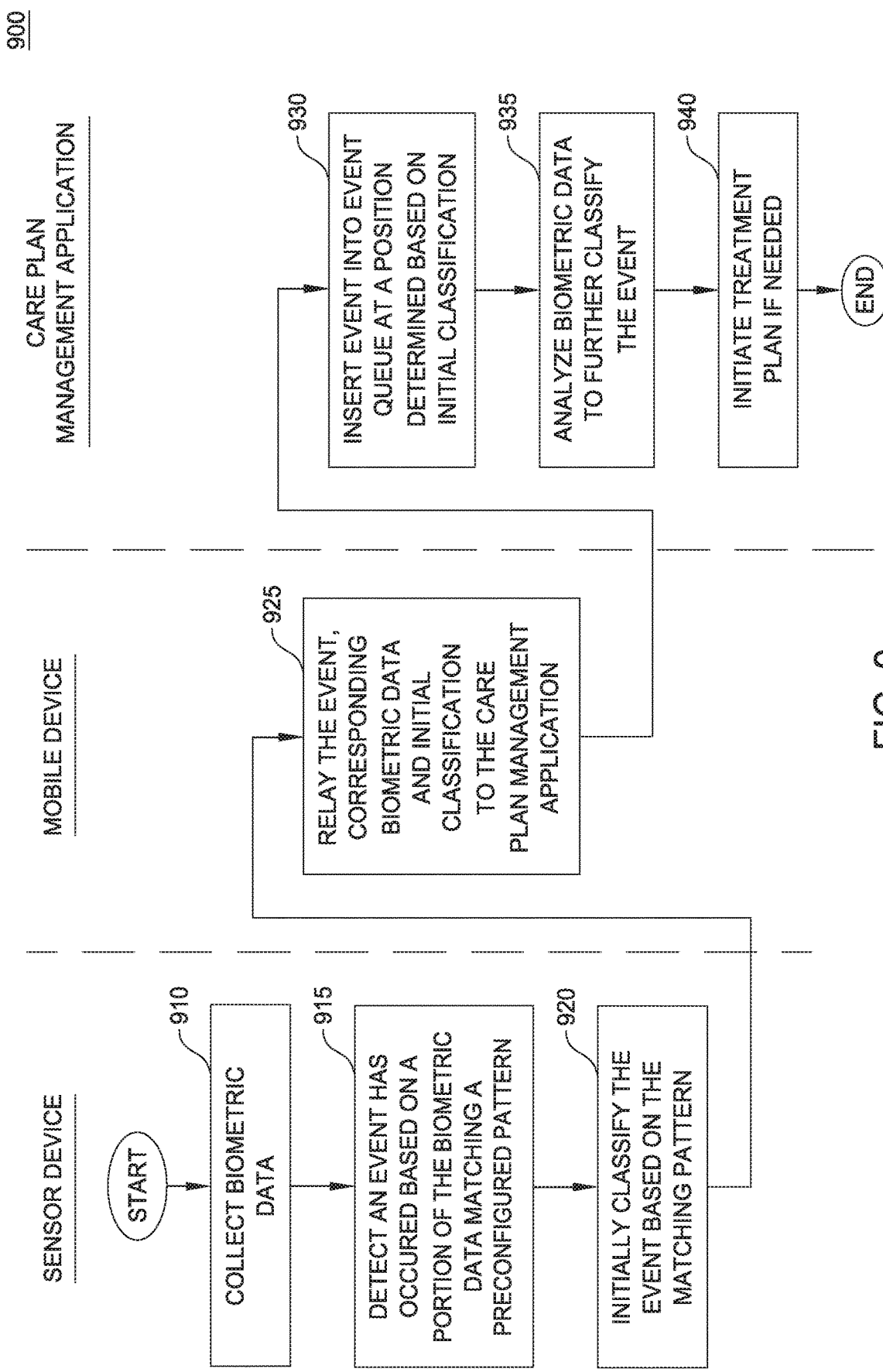
FIG. 9 is a flow diagram illustrating a method of administering a care plan using an event queue, according to one embodiment.

FIG. 9 is a flow diagram illustrating a method of administering a care plan using an event queue, according to one embodiment. As shown, the method 900 begins at block 910, where a sensor device 140 collects biometric data from the patient. As discussed above, a variety of different sensor devices 140 may be used in collecting data for the patient, and more generally any device suitable for collecting biometric data can be used. In the depicted method 900, the sensor device 140 further detects that an event has occurred based on a portion of the collected biometric data matching a preconfigured pattern (block 915). The sensor device 140 then classifies the event as a first type of event, based on the pattern that matches the collected biometric data (block 920).

In one embodiment, the sensor device 140 is configured to transmit the biometric data to the mobile device 135, and the mobile device 135 is configured to perform the pattern-matching analysis on the biometric data in order to detect occurrences of health-related events. Such an embodiment may be preferable, for instance, when the sensor device 140 lacks the capability to perform the analysis or is otherwise ill-suited for the task.

Returning to the method 900, the sensor device 140 transmits the event, along with the corresponding biometric data and initial classification, to the mobile device 135, which relays the information to the core plan management application (block 925). Of note, although the sensor device 140 is depicted as determining the initial classification in the method 900, more generally the initial classification can be determined by any suitable device (e.g., mobile device 135). Upon receiving the event and corresponding data, the core plan management application 111 inserts the event into an event queue at a position determined based on the initial classification of the event (block 930). For example, the core plan management application 111 could maintain a respective event queue for each patient being monitored, and the core plan management application 111 could generally insert events into the event queue in the order they are detected. However, in the event the initial classification of the event indicates that the event is a higher priority event, the core plan management application 111 could insert the event into the event queue at a position closer to the front of the queue where the event will be processed more quickly, while urgent priority events could be inserted at a position at the front of the event queue ahead of all lower priority events. Likewise, moderate priority events could be placed at a position within the event queue ahead of lower priority events in order of processing but behind higher priority events. Doing so allows the core plan management application 111 to tailor the processing order of the events to the anticipated severity of each event.

At some subsequent point in time, the core plan management application 111 processes the event as the next event in the event queue in order to further classify the event by analyzing the corresponding biometric data (block 935). That is, the core plan management application 111 continues processing events from the event queue in their inserted order until the inserted event in question is processed. Generally, the type of analysis performed in processing the event depends on the type of the event and the corresponding biometric data. As an example, the sensor device 140 could initially classify the event as a cardiac event, based on monitored ECG data collected from the patient matching a predetermined pattern indicative of a cardiac event. The core plan management application 111 could then process the collected ECG data to determine which specific sub-classification of cardiac event occurred. As such processing can be significantly more computationally intensive than the initial pattern matching, the core plan management application 111 may be better suited for performing the complex analysis (e.g., utilizing a data center or cloud computing environment's vast resources) than the sensor device 140 or even the mobile device 135.

Generally, the core plan management application 111 can further classify the event in a variety of different ways. In some circumstances, the core plan management application 111 may reclassify the event as a different type of event, rather than a sub-classification of the initial classification. For example, although the sensor device 140 may initially classify the event as a hyperglycemic event, the core plan management application 111 could further analyze the collected biometric data and determine that the portion of biometric data is instead indicative of an occurrence of normal blood sugar levels for the patient. Moreover, in other circumstances, the core plan management application 111 could analyze the biometric data and could determine that the data is actually not indicative of any recognizable event. In such a scenario, the core plan management application 111 could simply discard the event as a false positive. And in other circumstances, the core plan management application 111 may simply determine the initial classification of the event was the correct classification and that no further classification is needed or can be made.

Once the core plan management application 111 has further classified the event, the core plan management application 111 initiates a treatment plan based on the event as needed (block 940), and the method 900 ends. For example, a treatment plan for a low severity cardiac event may include transmitting instructions for the patient to sit down and perform breathing exercises for a period of time in order to see if the patient's biometric markers and any related symptoms improve. As another example, the treatment plan for a higher severity cardiac event may include alerting emergency personnel as to the patient's current condition. As yet another example, the treatment plan for a particular event may simply include annotating a patient log for the patient to mark the occurrence of the event for subsequent review by the patient's care provider. Moreover, in other circumstances, the core plan management application 111 may determine that the biometric data was incorrectly identified by the sensor device 140 as an occurrence of an event and that no treatment plan is needed since no event actually occurred.

Figure 10:
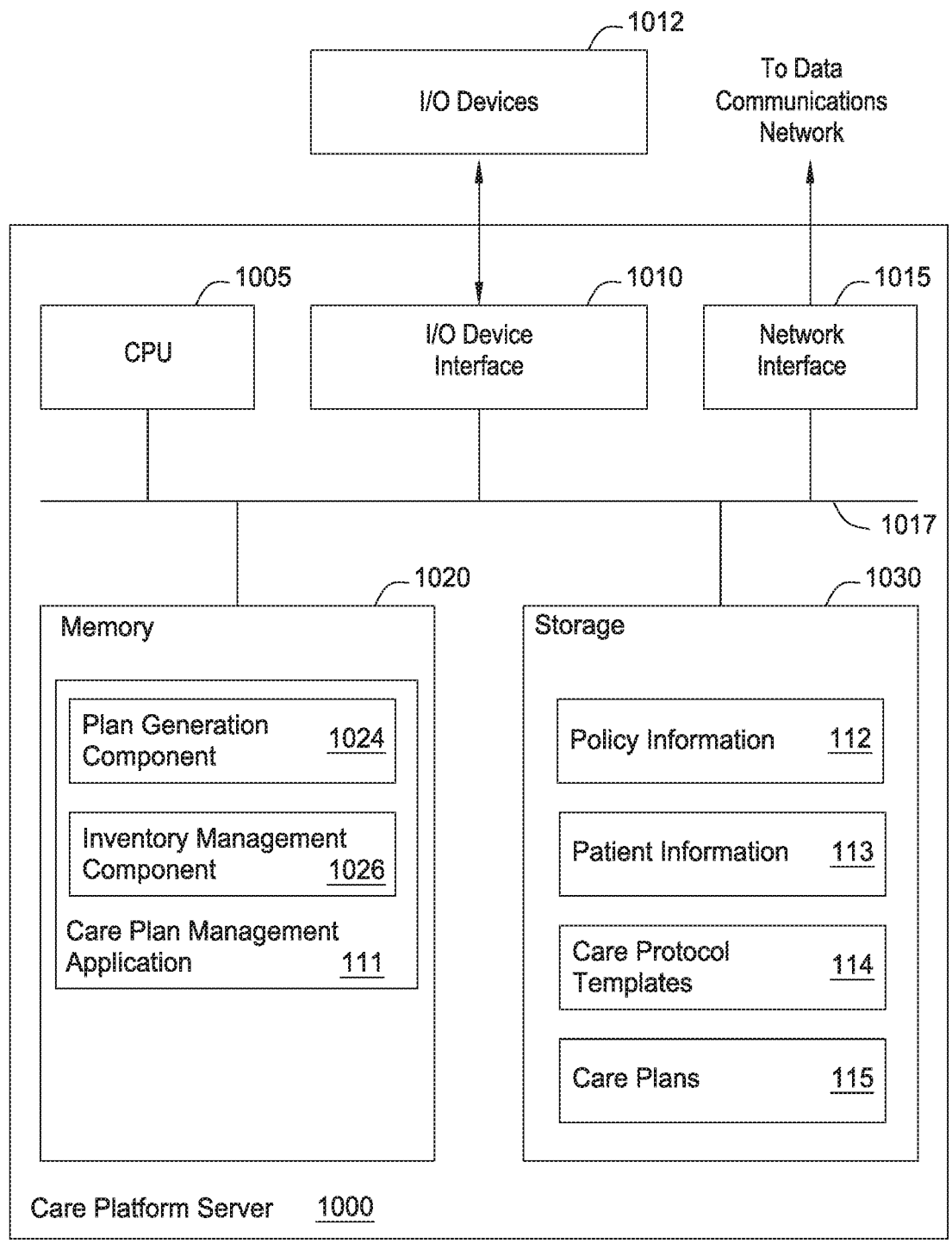
FIG. 10 illustrates a care platform server configured to administer a care plan, according to one embodiment.

FIG. 10 illustrates a care platform server 1000 configured to generate a care plan that may be customized for an individual, according to one embodiment. As shown, the care platform server 1000 includes, without limitation, a central processing unit (CPU) 1005, a network interface 1015, a memory 1020, and storage 1030, each connected to a bus 1017. The care platform server may also include an I/O device interface 1010 connecting I/O devices 1012 (e.g., keyboard, display and mouse devices) to the care platform server 1000. Further, in context of this disclosure, the computing elements shown in the care platform server 1000 may correspond to a physical computing system (e.g., a system in a data center) or may be a virtual computing instance executing within a computing cloud.

CPU 1005 retrieves and executes programming instructions stored in memory 1020 as well as stores and retrieves application data residing in the storage 1030. The bus 1017 is used to transmit programming instructions and application data between CPU 1005, I/O devices interface 1010, storage 1030, network interface 1017, and memory 1020. Note, CPU 1005 is included to be representative of a single CPU, multiple CPUs, a single CPU having multiple processing cores, and the like. Memory 1020 is generally included to be representative of a random access memory. Storage 1030 may be a disk drive storage device. Although shown as a single unit, storage 1030 may be a combination of fixed and/or removable storage devices, such as fixed disc drives, removable memory cards, or optical storage, network attached storage (NAS), or a storage area-network (SAN).

Illustratively, memory 1020 includes a care plan management application 1022. And storage 1030 includes policy information 112, patient information 113, care protocol templates 114, and care plans 115. The care plan management application 1022 further includes a plan generation component 1024 and an inventory management component 1026. The plan generation component 1024 is generally configured to create a care plan 115 based on a received selection of care protocol templates 114, received customizations of the selected templates 114, policy information 112, and patient information 113.

Each care protocol template 114 provides a set of tasks, thresholds, and other metrics targeted towards treating a certain condition (e.g., diabetes, heart issues, etc.). Although care protocol templates 114 are general in nature, a care provider may modify the care protocol template 114 to be specific to a given patient (e.g., by adding, editing, and removing tasks). The plan generation component 1024 may resolve conflicts between overlapping tasks and thresholds based on conflict resolution rules associated with each task and threshold.

The inventory management component 1026 maintains an inventory of available monitoring devices and can further maintain associations of particular monitoring devices issued by a care provider (e.g., body sensors, weight scales, etc.) with respective patients. Further, the inventory management component 1026 can associate a care plan with a mobile device application of the patient to ensure that the plan generation component 205 sends the care plan to the correct mobile device.

Policy information 112 includes various guidelines (e.g., set by a hospital, standards organization, insurance companies, etc.) that each care protocol assigned by a care provider should adhere to. For example, the policy information 112 may specify acceptable bounds of medication to instruct a patient to take. The plan generation component 1024 may enforce the policy information 112 when generating a care plan 115, e.g., by raising a flag for a care provider to review in the event that the care provider customizes a care protocol in a way that violates the policy information 112.

Patient information 113 includes patient medical histories and charts. Such histories and charts may provide treatment information that the plan generation component 1024 may use to identify effective and detrimental treatments (e.g., medications, exercises, etc.) applied to a patient in the past. Once identified, the plan generation component 1024 may modify a care plan 115 based on the identified information.

One embodiment of the present disclosure is implemented as a program product for use with a computer system. The program(s) of the program product defines functions of the embodiments (including the methods described herein) and can be contained on a variety of computer-readable storage media. Examples of computer-readable storage media include (i) non-writable storage media (e.g., read-only memory devices within a computer such as CD-ROM or DVD-ROM disks readable by an optical media drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present disclosure, are embodiments of the present disclosure. Other examples media include communications media through which information is conveyed to a computer, such as through a computer or telephone network, including wireless communications networks.

In general, the routines executed to implement the embodiments of the present disclosure may be part of an operating system or a specific application, component, program, module, object, or sequence of instructions. The computer program of the present disclosure is comprised typically of a multitude of instructions that will be translated by the native computer into a machine-readable format and hence executable instructions. Also, programs are comprised of variables and data structures that either reside locally to the program or are found in memory or on storage devices. In addition, various programs described herein may be identified based upon the application for which they are implemented in a specific embodiment of the disclosure. However, it should be appreciated that any particular program nomenclature that follows is used merely for convenience, and thus the present disclosure should not be limited to use solely in any specific application identified and/or implied by such nomenclature.

As described, embodiments herein provide techniques for generating a health care plan that may be customized for an individual. Advantageously, the care plans that the care platform generates may be tailored to a specific individual. Doing so allows a care provider to provide a more detailed and effective approach to treating a patient's condition than a care plan that consists of generalized tasks. Further, because the care plan may be tied to mobile and sensor devices of the patient, the care platform may monitor the progress of the patient's adherence to the care plan, allowing for further customization of the care plan as necessary.

While the foregoing is directed to embodiments of the present disclosure, other and further embodiments of the disclosure may be devised without departing from the basic scope thereof, and the scope thereof is determined by the claims that follow.

What is claimed is:

1. A method for administering a care plan, comprising:
receiving, at a care plan management system using a communication network, biometric data collected by a monitoring device and comprising a first event classified by a remote device as a first type of event;
determining, at the care plan management system, a relative processing priority for the first event based on the first type;
processing the first event, at the care plan management system, based on the relative processing priority, the processing comprising re-classifying the first event as a second type of event, wherein the re-classification is more computationally intensive than the classification by the remote device; and
initiating at least one treatment task specified in the care plan, using a computer processor, and based on the re-classified first event.

2. The method of claim 1, wherein the second type of event is a sub-classification of the first type of event.

3. The method of claim 2, wherein the re-classifying the first event as the second type of event comprises determining that at least a portion of the biometric data matches a preconfigured data pattern.

4. The method of claim 2, wherein the first type of event comprises a cardiac event and wherein the second type of event comprises a sub-classification of the cardiac event.

5. The method of claim 1, wherein the biometric data is received from a mobile device configured to communicate with the monitoring device, wherein the mobile device facilitates communication between the monitoring device and the care plan management system, and wherein the remote device comprises at least one of the mobile device or the monitoring device.

6. The method of claim 5, wherein the remote device comprises the monitoring device.

7. The method of claim 5, wherein initiating the at least one treatment task further comprises:
outputting a graphical user interface using a display device of the mobile device requesting symptom information from a patient;
receiving a selection of one or more symptoms via the graphical user interface; and
determining one or more actions specified by the care plan to perform, based on the received selection of one or more symptoms and the collected biometric data, wherein initiating the at least one treatment task is performed further responsive to determining that at least one symptom condition specified in the care plan is satisfied by the received selection of one or more symptoms.

8. The method of claim 7, wherein the determined one or more actions comprises at least one of requesting the patient perform one or more tasks, transmitting educational content to the mobile device for review by the patient, or generating an alert message describing a current state of the patient.

9. The method of claim 1, wherein the care plan further specifies a plurality of phases, wherein only one of the plurality of phases is active at a time, wherein each of the plurality of phases comprises:
a respective two or more of a plurality of observation metrics;
a respective two or more of a plurality of assigned tasks for the patient to perform; and
conditional logic that, when satisfied while the phase is active, indicates that another one of the plurality of phases should become active.

10. The method of claim 1, wherein processing the first event, at the care plan management system, based on the relative processing priority comprises:
inserting the first event into an event queue at a position determined based on the relative priority of the first event; and
retrieving the first event from the event queue, based on the position.

11. A non-transitory computer-readable medium containing computer program code that, when executed, performs an operation for administering a care plan, the operation comprising:
receiving, at a care plan management system using a communication network, biometric data collected by a monitoring device and comprising a first event classified by a remote device as a first type of event;
determining, at the care plan management system, a relative processing priority for the first event based on the first type;
processing the first event, at the care plan management system, based on the relative processing priority, the processing comprising re-classifying the first event as a second type of event, wherein the re-classification is more computationally intensive than the classification by the remote device; and
initiating at least one treatment task specified in the care plan, based on the re-classified first event.

12. The non-transitory computer-readable medium of claim 11, wherein the re-classifying the first event as the second type of event comprises determining that at least a portion of the biometric data matches a preconfigured data pattern.

13. The non-transitory computer-readable medium of claim 11, wherein the first type of event comprises a cardiac event and wherein the second type of event comprises a sub-classification of the cardiac event.

14. The non-transitory computer-readable medium of claim 11, wherein the biometric data is received from a mobile device configured to communicate with the monitoring device, wherein the mobile device facilitates communication between the monitoring device and the care plan management system, and wherein the remote device comprises at least one of the mobile device or the monitoring device.

15. The non-transitory computer-readable medium of claim 14, wherein initiating the at least one treatment task further comprises:

outputting a graphical user interface using a display device of the mobile device requesting symptom information from a patient;

receiving a selection of one or more symptoms via the graphical user interface; and determining one or more actions specified by the care plan to perform, based on the received selection of one or more symptoms and the collected biometric data, wherein initiating the at least one treatment task is performed further responsive to determining that at least one symptom condition specified in the care plan is satisfied by the received selection of one or more symptoms.

16. The non-transitory computer-readable medium of claim 11, wherein processing the first event, at the care plan management system, based on the relative processing priority comprises:

inserting the first event into an event queue at a position determined based on the relative priority of the first event; and retrieving the first event from the event queue, based on the position.

17. A system for administering a care plan, comprising:

a monitoring device;

a care plan management system; and a mobile device that facilitates communication between the monitoring device and the care plan management system, wherein the care plan management system is configured to:

receive, using a communication network, biometric data collected by the monitoring device and comprising a first event classified as a first type of event by at least one of the monitoring device or the mobile device;

determine a relative processing priority for the first event based on the first type; and process the first event based on the relative processing priority, the processing comprising re-classifying the first event as a second type of event, wherein the re-classification is more computationally intensive than the classification as the first type of event; and wherein the system is configured to:

initiate at least one treatment task specified in the care plan, based on the re-classified first event.

18. The system of claim 17, wherein the first event is classified as the first type of event by the monitoring device.

19. The system of claim 17, wherein the initiating the at least one treatment task further comprises:

outputting a graphical user interface using a display device of the mobile device requesting symptom information from a patient;

receiving a selection of one or more symptoms via the graphical user interface; and determining one or more actions specified by the care plan to perform, based on the received selection of one or more symptoms and the collected biometric data, wherein initiating the at least one treatment task is performed further responsive to determining that at least one symptom condition specified in the care plan is satisfied by the received selection of one or more symptoms.

20. The system of claim 17, wherein the processing the first event based on the relative processing priority comprises:

inserting the first event into an event queue at a position determined based on the relative priority of the first event; and retrieving the first event from the event queue, based on the position.

* * * * *